United States Patent
Pivot et al.

(10) Patent No.: US 11,872,071 B2
(45) Date of Patent: Jan. 16, 2024

(54) METHOD FOR CORRECTING A SPECTRAL IMAGE

(71) Applicants: COMMISSARIAT A L'ENERGIE ATOMIQUE ET AUX ENERGIES ALTERNATIVES, Paris (FR); CENTRE NATIONAL DE LA RECHERCHE SCIENTIFIQUE, Paris (FR); INSTITUT NATIONAL DES SCIENCES APPLIQUEES DE LYON, Villeurbanne (FR)

(72) Inventors: Odran Pivot, Grenoble (FR); Joachim Tabary, Grenoble (FR); Clarisse Fournier, Grenoble (FR); Jean Michel Letang, Villeurbanne (FR); Simon Rit, Villeurbanne (FR)

(73) Assignees: COMMISSARIAT A L'ENERGIE ATOMIQUE ET AUX ENERGIES ALTERNATIVES, Paris (FR); CENTRE NATIONAL DE LA RECHERCHE SCIENTIFIQUE, Paris (FR); INSTITUT NATIONAL DES SCIENCES APPLIQUEES DE LYON, Villeurbanne (FR)

( * ) Notice: Subject to any disclaimer, the term of this patent is extended or adjusted under 35 U.S.C. 154(b) by 309 days.

(21) Appl. No.: 17/283,446

(22) PCT Filed: Oct. 7, 2019

(86) PCT No.: PCT/FR2019/052376
§ 371 (c)(1),
(2) Date: Apr. 7, 2021

(87) PCT Pub. No.: WO2020/074820
PCT Pub. Date: Apr. 16, 2020

(65) Prior Publication Data
US 2021/0364663 A1 Nov. 25, 2021

(30) Foreign Application Priority Data
Oct. 9, 2018 (FR) .................................. 1859368

(51) Int. Cl.
*A61B 6/00* (2006.01)
*G01N 23/041* (2018.01)
(Continued)

(52) U.S. Cl.
CPC .............. *A61B 6/5282* (2013.01); *A61B 6/06* (2013.01); *A61B 6/4035* (2013.01);
(Continued)

(58) Field of Classification Search
CPC ........... A61B 6/06; A61B 6/4035; A61B 6/42; A61B 6/4208; A61B 6/4233;
(Continued)

(56) References Cited

U.S. PATENT DOCUMENTS 6,639,964 B2 * 10/2003 Schneider .............. A61B 6/032
378/7
7,463,712 B2 * 12/2008 Zhu ........................ A61B 6/583
378/7
(Continued)

FOREIGN PATENT DOCUMENTS

EP 3 153 888 A1 4/2017

OTHER PUBLICATIONS

International Search Report dated Jan. 30, 2020 in PCT/FR2019/052376 filed on Oct. 7, 2019, 3 pages.
(Continued)

*Primary Examiner* — Allen C. Ho
(74) *Attorney, Agent, or Firm* — Oblon, McClelland, Maier & Neustadt, L.L.P.

(57) ABSTRACT

The invention concerns a method for processing energy spectra of radiation transmitted by an object irradiated by an
(Continued)

ionising radiation source, in particular X-ray radiation, for medical imaging or non-destructive testing applications. The method uses a detector comprising a plurality of pixels, each pixel being capable of acquiring a spectrum of the radiation transmitted by the object. The method makes it possible, based on a plurality of detected spectra, to estimate a spectrum, referred to as the scattering spectrum, representative of radiation scattered by the object. The estimation involves taking into account a spatial model of the scattering spectrum. Each acquired spectrum is corrected taking into account the estimated scattering spectrum. The invention makes it possible to reduce the influence of the scattering, by the object, of the spectrum emitted by the source.

13 Claims, 5 Drawing Sheets

(51) Int. Cl.
| | |
|---|---|
| *G01N 23/10* | (2018.01) |
| *G01N 23/18* | (2018.01) |
| *G01N 23/20066* | (2018.01) |
| *G01N 23/201* | (2018.01) |
| *G01T 1/16* | (2006.01) |
| *G01T 1/36* | (2006.01) |
| *G01N 23/20091* | (2018.01) |
| *G01T 1/29* | (2006.01) |
| *A61B 6/06* | (2006.01) |
| *G01N 23/04* | (2018.01) |
| *G01N 23/046* | (2018.01) |

(52) U.S. Cl.
CPC ............ *A61B 6/4208* (2013.01); *A61B 6/482* (2013.01); *A61B 6/483* (2013.01); *A61B 6/5258* (2013.01); *A61B 6/585* (2013.01); *G01N 23/04* (2013.01); *G01N 23/046* (2013.01); *G01N 23/201* (2013.01); *G01N 23/20066* (2013.01); *G01N 23/20091* (2013.01); *G01T 1/295* (2013.01); *G01T 1/2914* (2013.01); *G01T 1/36* (2013.01); *G01N 2223/401* (2013.01)

(58) Field of Classification Search
CPC ..... A61B 6/4241; A61B 6/4258; A61B 6/482; A61B 6/483; A61B 6/484; A61B 6/5258; A61B 6/5282; A61B 6/585; A61B 6/4266; A61B 6/4291; G01N 23/04; G01N 23/041; G01N 23/046; G01N 23/20008; G01N 23/20066; G01N 23/20091; G01N 23/201; G01N 23/10; G01N 23/18; G01T 1/16; G01T 1/1603; G01T 1/24; G01T 1/242; G01T 1/243; G01T 1/248; G01T 1/249; G01T 1/29; G01T 1/2907; G01T 1/2914; G01T 1/2921; G01T 1/2928; G01T 1/2935; G01T 1/295; G01T 1/2957; G01T 1/36; G21K 1/02; G21K 1/025; G21K 2207/00; G21K 2207/005
USPC .. 378/2, 5, 7, 16, 19, 62, 86–90, 98.8, 98.9, 378/147, 149, 57, 58, 63, 207; 250/370.09
See application file for complete search history.

(56) References Cited

U.S. PATENT DOCUMENTS

| | | | | |
|---|---|---|---|---|
| 7,504,635 | B2* | 3/2009 | Ramsden | G01T 1/1642 |
| | | | | 250/369 |
| 7,570,732 | B2* | 8/2009 | Stanton | A61B 6/466 |
| | | | | 378/7 |
| 7,907,697 | B2* | 3/2011 | Maltz | G06T 11/005 |
| | | | | 378/7 |
| 8,139,709 | B2* | 3/2012 | Noo | A61B 6/583 |
| | | | | 378/19 |
| 8,326,011 | B2* | 12/2012 | Star-Lack | G06T 7/0012 |
| | | | | 378/7 |
| 8,488,902 | B2* | 7/2013 | Bertram | G06T 5/20 |
| | | | | 382/274 |
| 9,128,194 | B2* | 9/2015 | Zou | A61B 6/5205 |
| 9,285,326 | B2* | 3/2016 | Gagnon | A61B 6/5282 |
| 9,330,458 | B2* | 5/2016 | Star-Lack | A61B 6/5282 |
| 9,687,207 | B2* | 6/2017 | Zou | G01T 1/2985 |
| 10,079,078 | B2* | 9/2018 | Sossin | G21K 1/10 |
| 10,107,768 | B2* | 10/2018 | Brady | G01N 23/20008 |
| 10,499,869 | B2* | 12/2019 | Petschke | A61B 6/032 |
| 10,983,070 | B2* | 4/2021 | Paulus | G01N 23/04 |
| 11,060,987 | B2* | 7/2021 | Lu | G06N 20/00 |
| 11,243,327 | B2* | 2/2022 | Scoullar | G01N 23/12 |
| 11,340,363 | B2* | 5/2022 | Daerr | G01T 1/2928 |
| 2007/0242794 | A1 | 10/2007 | Stanton et al. | |
| 2007/0268997 | A1 | 11/2007 | Zhu et al. | |
| 2009/0274272 | A1 | 11/2009 | Stanton et al. | |

OTHER PUBLICATIONS

French Preliminary Search Report (with English translation of Categories of Cited Documents) dated Aug. 14, 2019 in French Application 1859368 filed on Oct. 9, 2018, 4 pages.
Sossin, A. et al., "Characterizing the behavior of scattered radiation in multi-energy x-ray imaging," Nuclear Instruments and Methods in Physics Research A, vol. 850, 2017, pp. 25-34, XP029917295.
Katsevich, A. et al., "High-Quality 3-D MicroCT Imaging of Source Rocks—Novel Methodology to Measure and Correct for X-Ray Scatter," Unconventional Resources Technology Conference, URTeC: 2902457, 2018, pp. 1-20, XP055612288.

* cited by examiner

METHOD FOR CORRECTING A SPECTRAL IMAGE

TECHNICAL FIELD

The technical field of the invention is correction of a spectral image formed by a pixelated detector. The invention may notably be applied in the field of X-ray or gamma-ray imaging, for example in the context of assisting with medical diagnosis.

PRIOR ART

The inspection of objects with X-rays, in the medical or industrial field, is very widespread. Existing methods consist in placing an object between a source of radiation and a detector, then in irradiating the object using the source. The detector then forms an image, generally in two dimensions, of the radiation transmitted by the object. This image is representative of the attenuation, by the object, of the radiation emitted by the source.

The radiation transmitted by the object generally comprises a component resulting from scattering, by the object, of the radiation emitted by the source. The significance of this component increases as the energy of the radiation decreases and/or as the atomic number of the material from which the object is made increases. This component, which is commonly referred to as scattered radiation, hinders interpretation of the images, because it is only indirectly related to the attenuation by the object. In addition, whereas the non-scattered radiation, which is referred to as the primary radiation, propagates between the source and the detector along a rectilinear path, the scattered radiation may originate from any point in the object, and the angle of its path, from this point of origin, may be one of a distribution of various angles. It is therefore sought to estimate this scattered component, so as to extract it from the signal measured by the detector, before the images are processed with a view to interpreting them.

Numerical simulation tools allow the primary radiation and the scattered radiation having passed through an analyzed object to be determined. One example is given in the publication Sossin A. "Fast scattering simulation tool for multi-energy x-ray imaging" Nuclear Instruments and Methods in Physics Research, A 802 (2015) 60-66. Such tools facilitate the development of radiography or tomography systems.

In the field of medical imaging, many methods have been developed with a view to making an attempt to estimate and to decrease the prevalence of the scattered radiation, so as to obtain an image that is essentially representative of the non-scattered radiation, called primary radiation, that propagates between the source and the object in a rectilinear direction. For example, patent EP3153888 describes a method in which a mask, defining a checkerboard pattern, is placed between a source of radiation and a pixelated detector. Two acquisitions are made, respectively with and without a mask. A comparison of the two acquisitions allows the spectrum of the scattered component of the radiation detected by each pixel of the detector to be estimated. Although such a method is effective, it requires two acquisitions, one with and one without a mask, to be carried out, this requiring the mask to be designed to be retractable. In addition, performing two acquisitions would seem to be at odds with the need to decrease dosimetry during medical examinations.

The inventors propose an alternative method that allows the spectrum of radiation that is scattered by an irradiated object, and that propagates to the pixels of a spectrometric detector, to be estimated. The spectrum thus estimated is used to correct the spectrum of the radiation detected by each pixel. The method does not require performing two acquisitions, one with and one without a mask.

SUMMARY OF THE INVENTION

A first subject of the invention is a method for correcting a spectral image formed by ionizing electromagnetic radiation transmitted by an object, the object being placed between a radiation source and a detector, the radiation source being able to emit ionizing electromagnetic radiation, called the incident radiation, toward the object;

the detector comprising pixels, each pixel being configured to detect radiation transmitted by the object to the detector, and to measure a spectrum thereof, the transmitted radiation comprising scattered radiation, caused by scattering of the incident radiation in the object, and primary radiation;

a mask being interposed between the source and the detector, the mask comprising absorbent elements, which are able to attenuate one portion of the incident radiation, the projection of each absorbent element onto the detector forming one shadow region, such that the detector comprises a plurality of shadow regions that are spaced apart from one another, each shadow region comprising at least one pixel;

the method comprising the following steps:
a) irradiating the object and measuring, by means of the pixels of the detector, an energy spectrum representative of the radiation transmitted by the object;
b) defining a spatial model of the spectrum of the scattered radiation, so as to obtain, for various pixels of the detector, an estimate of the spectrum of the scattered radiation detected by each pixel, the spatial model being defined by parameters;
c) taking into account a cost function, the cost function being defined for various pixels and taking into account, at the level of each pixel, a spatial variation in an estimate of the spectrum of the primary radiation transmitted by the object in the absence of the mask, the estimate of the spectrum of the primary radiation in the absence of the mask being obtained by comparing, for each pixel:
the spectrum measured by the pixel in step a);
an estimate of the spectrum of the scattered radiation, which estimate is obtained using the spatial model resulting from step b);
d) determining the parameters, of the spatial model, for which the cost function is minimal or maximal or close to a preset value;
e) for at least one pixel, estimating the scattered-radiation spectrum reaching the pixel, by applying the parameters of the spatial model that were determined in step d).

The method may comprise a step:
f) for at least one pixel, correcting the spectrum measured in step a) using the estimate of the spectrum of the scattered radiation resulting from step e), so as to obtain a corrected spectrum corresponding to an estimate of the spectrum of the primary radiation reaching the pixel.

In step f), the corrected spectrum may correspond to an estimate of the spectrum of the primary radiation reaching the pixel with no mask placed between the source and the detector, this being a preferred variant, or with the mask present.

By function defined for various pixels, what is meant is a function established on the basis of the spectrum measured by various pixels.

By radiation transmitted by the object, or radiation reaching a pixel, or radiation that propagates to the pixel, what is meant is radiation incident on the pixel or radiation detected by the pixel. The passage between the radiation incident on the pixel and the radiation detected by the pixel is established by taking into account a response function of the pixel. The response function may notably be represented in matrix form.

The mask may be placed between the source and the object. Alternatively, the mask may be placed between the object and the detector.

By spectrum representative of the radiation transmitted by the object, what is meant is a spectrum of the radiation transmitted by the object or a spectrum obtained from the spectrum of the radiation transmitted by the object. It may for example be a question of a spectrum resulting from a normalization of the spectrum of the radiation transmitted by the object.

Preferably, the pixels of the detector lie in a detection plane; the spatial model is then defined at least along two axes defining the detection plane.

According to one embodiment:
step a) is implemented in a plurality of configurations, each configuration being associated with one orientation of the detector with respect to the object, so as to measure, by means of each pixel, spectra corresponding to various orientations;
the spatial model defined in step b) takes into account a variation in the spectrum of the scattered radiation as a function of the orientation of the detector with respect to the object.

In step C), the primary spectrum transmitted by the object to each pixel, in the absence of the mask, may be estimated by applying a correction matrix, defined for each pixel, to a difference between:
the spectrum measured by the pixel in step a);
an estimate of the spectrum of the scattered radiation, which estimate is obtained using the parametric model resulting from step b).

The correction matrix may be obtained in a calibrating phase, with no object between the radiation source and the detector, according to the following calibrating steps:
cal-i) irradiating the detector with and without the mask interposed between the source and the detector, so as to obtain, for each pixel, a full-flux spectrum and a masked spectrum, respectively;
cal-ii) taking into account a parametric function in order to determine terms of the matrix, the parametric function depending on parameters;
cal-iii) taking into account the full-flux spectrum and the masked spectrum to determine the parameters of the parametric function, so as to determine the terms of the correction matrix.

The correction matrix is preferably triangular.

The spatial model of the scattered radiation may be expressed as a product:
of a matrix representative of a spatial distribution of the scattered radiation;
of a vector of parameters comprising the parameters of the spatial scattering model;
such that step d) comprises estimating the vector of parameters.

According to one embodiment, step b) comprises defining a spectral model of the scattered radiation, in order to take into account, in each pixel, a spectral variation of the scattered radiation, such that the spatial model and spectral model are defined by a vector of parameters. According to this embodiment, the spatial model and the spectral model of the scattered radiation may be expressed as a product:
of a matrix representative of a spatial distribution of the scattered radiation;
of a matrix representative of the spectral variation of the scattered radiation;
of the vector of parameters;
such that step d) comprises estimating the vector of parameters.

Each absorbent element of the mask is, preferably, able to absorb between 5% and 80% of the radiation to which it is exposed, in a predetermined energy band. The mask extending over an area, each absorbent element is preferably distant from another absorbent element by a distance of smaller than 1 cm.

According to one embodiment, step a) comprises normalizing the spectrum of radiation transmitted by the object and measured by the pixel, by a spectrum measured by the pixel with no object placed between the source and the detector.

The method may be implemented by determining pixels of the detector that are considered to be relevant, the spectra measured by these pixels being given a higher weight in the computation of the cost function. Relevant pixels may be pixels adjacent to the shadow regions formed by the mask. They may also be located:
outside of the outlines bounding the object;
outside of internal structures of the object inducing a significant contrast in attenuation.

The cost function may comprise a weighting matrix, the coefficients of which tend to give, relative to pixels not considered to be relevant, a higher weight to a contribution of the relevant pixels.

A second subject of the invention is a non-transitory data-storage medium comprising instructions for executing steps b) to e) or b) to f) of the method according to the first subject of the invention, on the basis of the spectra measured in step a), these instructions being able to be executed by a microprocessor.

A third subject of the invention is a device for acquiring spectra of radiation transmitted by an object, comprising:
a radiation source, configured to emit ionizing electromagnetic radiation, called the incident radiation, toward said object;
a detector comprising pixels, each pixel being configured to detect radiation transmitted by the object to the detector, and to acquire a spectrum thereof;
a mask, able to be interposed between the source and the object, said mask comprising absorbent elements, which are able to absorb a portion of said incident radiation, and a projection of which onto the detector defines shadow regions that are distant from one another;
a processor, configured to receive the spectra acquired by each pixel, and to implement steps b) to e) or b) to f) of the method according to the first subject of the invention.

Other advantages and features will become more clearly apparent from the following description of particular embodiments of the invention, which are provided by way of nonlimiting examples, and which are shown in the figures listed below.

FIGURES

Figures 5A, 5B, 5C:
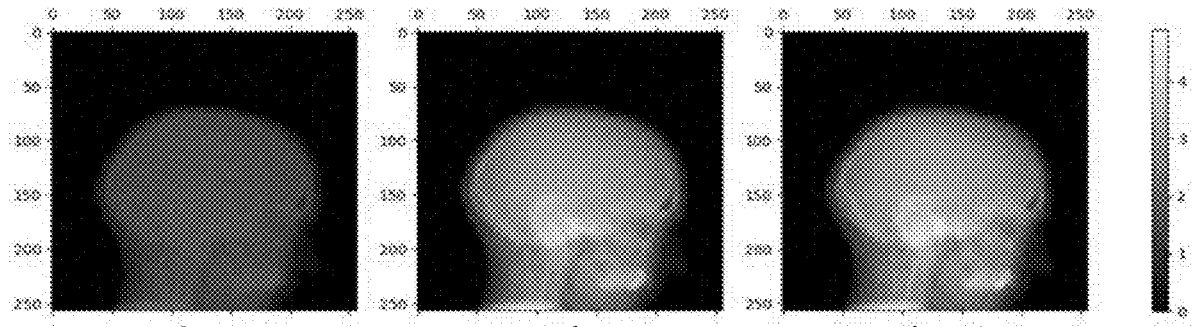
Figure 5D:
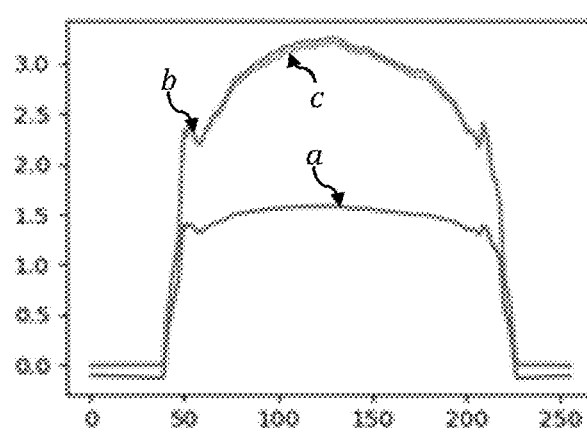
Figure 5E:
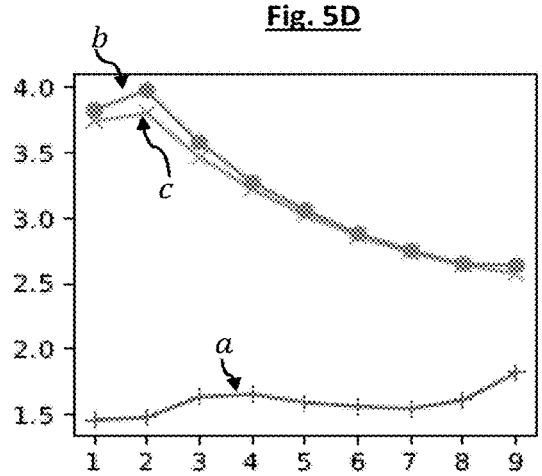

FIGS. 5A, 5B and 5C show results of modeling simulating an image of a modeled object, each image being based on spectra measured by the pixels of a detector, these spectra representing the total radiation, the primary radiation and the estimation of the primary radiation according to the invention, respectively. FIG. 5D shows a horizontal profile obtained on the basis of FIGS. 5A, 5B and 5C. FIG. 5E shows spectral attenuations obtained on the basis of the spectrum detected by the central pixel of FIGS. 5A, 5B and 5C, respectively.

DESCRIPTION OF PARTICULAR EMBODIMENTS

Figure 1A:
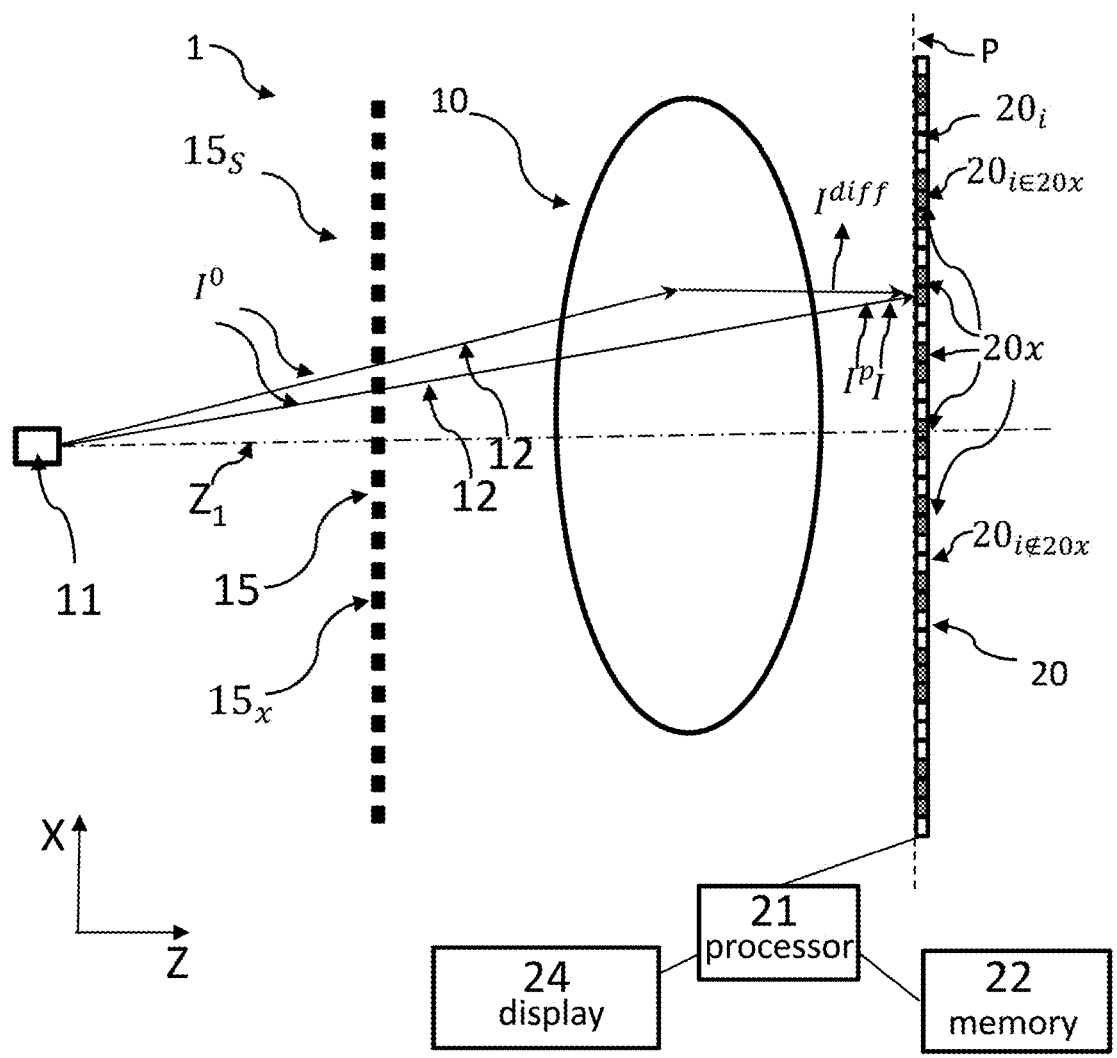
FIG. 1A shows a device allowing the invention to be implemented.

FIG. 1A represents one embodiment of a device 1 implementing a method according to the invention. A radiation source 11 emits ionizing electromagnetic radiation 12, called the incident radiation, toward an object 10. The object 10 is placed between the radiation source 11 and a radiation detector 20. The radiation detector 20 is a detector comprising pixels $20_i$ that are arranged in a plane, called the detection plane P. The index i designates a coordinate of each pixel in the detection plane P. The pixels $20_i$ may be arranged in a row but, in general, they are arranged in a regular two-dimensional matrix array. In this case, the index i represents a two-dimensional coordinate.

The object 10 may be a living biological tissue, for example a body part of an animal or of a human being. The device 1 is then a medical imaging device. The object 10 may also be an industrial part or a piece of luggage, the device 1 then being used for non-destructive testing or for security-related checks.

The term "ionizing electromagnetic radiation" designates electromagnetic radiation made up of photons of energy higher than 1 keV, and preferably lower than 5 MeV. The energy range of the ionizing radiation may be comprised between 1 keV and 2 MeV, but it most often lies between 1 keV and 150 keV or 300 keV. The ionizing radiation may be X-ray or y-ray radiation. Preferably, the source of ionizing radiation is poly-energetic, the incident radiation being emitted in an energy range generally extending over several tens or even hundreds of keV. It is notably a question of an X-ray emitting tube.

One portion of the photons of the incident radiation $I^0$, passes through the object 10 and reaches the radiation detector 20, without interacting with the object 10. These photons propagate to the radiation detector 20 without being deviated. These photons form a primary component, or the primary radiation $I^p$. Other photons of the incident radiation $I^0$ are absorbed in the object, for example via the photoelectric effect. Lastly, certain photons undergo a scattering interaction in the sample, such as inelastic Compton scattering or elastic Rayleigh scattering. The scattering, whether inelastic or elastic, causes a change in the direction of the photon.

Thus, the object 10 irradiated by the radiation source 11 transmits, to the radiation detector 20, radiation I, called transmitted radiation, which comprises:
- a direct component, or primary radiation, $I^p$, that did not interact with the object, and the path of which from the source is rectilinear;
- a scattered component $I^{diff}$, or scattered radiation, due to scattering of the incident radiation in the object.

The radiation I transmitted by the object 10 reaches the pixels $20_i$ of the radiation detector 20, each pixel detecting one portion of this radiation. The radiation transmitted by the object 10 and detected by a pixel $20_i$ is denoted $I_i$.

As mentioned with reference to the prior art, the scattered radiation $I^{diff}$ hinders interpretation of the measurements. Specifically, unlike the primary radiation $I^p$, the scattered radiation propagates, from the object to the detector, in a variable direction. Thus, one portion of the radiation collected by each pixel $20_i$ of the detector does not come directly from the radiation source 11, but results from the effect of scattering. However, the interpretation of the images is based on the attenuation of the incident radiation by the detector, said attenuation being obtained via a ratio, over a given energy range, between the intensity of the primary radiation $I^p$ and the intensity of the incident radiation $I^0$. A good interpretation of the images assumes knowledge of the intensity of the primary radiation $I^p$, whereas the radiation I transmitted by the object, and measured by the detector, comprises a sum of said primary radiation $I^p$ and of the scattered radiation $I^{diff}$.

Each pixel $20_i$ forms one radiation detector, comprising:
- a detector material that is able to interact with the photons of the radiation I transmitted by the object, this material being of scintillator type or, preferably, a semiconductor compatible with use at room temperature, such as CdTe or CdZnTe;
- an electronic circuit that is able to generate a signal the amplitude of which depends on, and is preferably proportional to, the energy deposited by each photon that interacts in the detector material;
- a spectrometry circuit that is able to establish an energy spectrum, denoted $S_i$, of the signals detected during a time period, called the acquisition period.

Thus, when the pixels are regularly arranged in a matrix array, each pixel is able to produce a spectrum $S_i$ of the radiation transmitted by the object. The detector is then able to form a plurality of images, each image representing a content of each spectrum in a determined energy range ΔE. Typically, each image contains the integral or the average value of each spectrum $S_i$ in said energy band. Spectral imaging is then spoken of, as the detector is both spatially and spectrally resolved.

Thus, under the effect of irradiation by the incident radiation $I^0$, the object 10 transmits radiation I, called transmitted radiation, to a pixelated spectrometric detector 20, each pixel $20_i$ of which is able to detect said transmitted radiation I and to form an energy spectrum $S_i$ from the radiation $I_i$ thus detected.

The term energy spectrum corresponds to a histogram of the amplitude of the signals detected during a period of acquisition of the spectrum. A relationship between the amplitude A and the energy E may be obtained via an energy calibration function g such that E=g(A), according to principles known to those skilled in the art. An energy spectrum $S_i$ is therefore a vector, each term $S_i(n)$ of which represents an amount of radiation detected by the pixel $20_i$ in an energy range $$E_n \pm \frac{\partial E}{2},$$

with $\partial E$ being the spectral width of each channel, n designating a channel number. To each channel n corresponds one energy $E_n$, or more exactly one energy range $$E_n \pm \frac{\partial E}{2}.$$

The energy spectrum $S_i$, measured by the pixel $20_i$, may be normalized by a spectrum $S_{0,i}$ measured by the pixel $20_i$ in the absence of any object, the latter spectrum representing the spectrum of the radiation $I^0$ emitted by the source. The spectrum $S_{0,i}$ measured by the pixel in the absence of any object is commonly designated by the term "full-flux spectrum". Thus, the spectrum $S_i$ is the spectrum measured by a pixel $20_i$, and optionally normalized by the spectrum $S_{0,i}$. The spectrum $S_{0,i}$ is preferably measured with no mask 15 placed between the source and the detector.

Neglecting noise, each energy spectrum $S_i$ may be considered to be a sum of a spectrum of the primary radiation, denoted $S_i^p$, and of a spectrum $S_i^{diff}$ of the scattered radiation. Thus, $S_i \approx S_i^p + S_i^{diff}$ (1). The sign means equal excluding noise, this noise notably resulting from the radiation source, from the detector or from so-called pile-up effects, which occur when two incident photons are detected simultaneously.

The device also comprises a mask 15, which is arranged between the source 11 and the detector 20 and, in this example, between the source 11 and the object 10, this being the preferred configuration. This mask comprises absorbent elements $15_x$ that are spatially distributed over an area $15_s$ over which the mask extends. Each absorbent element is able to partially attenuate one portion of the incident radiation $I^0$ produced by the radiation source. The absorbent elements are distributed discretely, such that the space between two adjacent absorbent elements is less absorbent than said absorbent elements. In other words, the absorbent elements define a discrete spatial distribution of attenuations $att_{15}^x$, $att_{15}^{x'}$ such that, between two adjacent elements $15_x$, $15_{x'}$, the attenuation $att_{15}^0$ is lower than the attenuation $att_{15}^x$, $att_{15}^{x'}$ associated with each absorbent element.

The meaning of the term attenuation is known to those skilled in the art. The attenuation may be expressed using the expression $$att_{15}^x(E) = -\ln\left[\frac{I^x(E)}{I^0(E)}\right],$$

where $I^0(E)$ designates an intensity, at an energy E, of radiation $I^0$ incident on an absorbent element $15_x$ and $I^x(E)$ designates an intensity, at said energy E, of radiation $I^x$ transmitted by the absorbent element $15_x$.

The attenuation may be expressed as a function of a linear attenuation coefficient $\mu(E)$ that is dependent on energy E and on the material from which the mask is made, according to the expression:

$$att_{15}^x(E) = -\mu(E)\ell_x,$$

$\ell_x$ designating the thickness of the attenuating element $15_x$ passed through.

Generally, the interposition of the mask 15 between the source 11 and the detector 20 must not significantly modify the scattered radiation reaching the detector, with respect to a configuration without the mask. Thus, preferably, each absorbent element has an attenuation, such as defined above, comprised between 0.05 and 1.5, at one of the energies of the energy range in which the incident radiation $I^0$ is emitted, or at the mean energy of this energy range. Thus, neglecting scattering, each absorbent element attenuates, preferably, between 5% and 80% of the incident radiation $I^0$ produced by the source and/or passing through the mask in the space extending between the absorbent elements of the mask. Preferably, the attenuation is lower than 1 or even lower than 0.5 and preferably lower than 0.3. Thus, each absorbent element respectively absorbs less than 60%, or less than 40%, and preferably less than 30% of the radiation produced by the source, or of the radiation passing between the absorbent elements of the mask. Below an attenuation equal to 0.05, corresponding to an attenuation of 5% of the radiation produced by the source, the inventors consider that the attenuation is insufficient. In other words, the mask 15 therefore allows a contrast in attenuation to be established between the absorbent elements $15_x$ and the space lying between said absorbent elements, the latter absorbing between 5% and 30%, or even 40%, or even more of the radiation that passes through said space.

In addition or alternatively, it is possible to define an overall attenuation of the mask 15 taking the form of a product of a fill factor multiplied by the percentage of the incident radiation absorbed by the mask, the latter being determined at an energy of the energy range of incident radiation $I^0$ emitted by the radiation source 11, or at a mean energy of this range. The fill factor corresponds to a ratio between the area of the mask occupied by the set of absorbent elements $15_x$ and the total area of the mask. The overall attenuation of the mask, thus defined, is preferably higher than 0.5% and lower than 20%. Thus, a mask that meets this condition may have a fill factor equal to 0.2, each element $15_x$ of the mask absorbing 10% of the incident radiation, this giving, for the mask, an overall attenuation, such as defined above, equal to 0.02 (2%).

Each absorbent element may have any shape, but at least one dimension, in a direction of the area $15_s$ over which it extends, is smaller than 5 mm, and preferably smaller than 2 mm or even 1 mm. In all of the embodiments described above, the mask preferably lies in an XY plane parallel to a plane in which the pixels of the detector lie.

The spacing between two adjacent absorbent elements, in the mask, may be smaller than 5 mm, and is preferably comprised between 1 mm and 5 mm. Generally, the spacing between two adjacent absorbent elements, after projection onto the detector 20, is advantageously comprised between 1 and 10 cm, and is preferably smaller than 5 cm or 3 cm. As described below, the projection of each absorbent element $15_x$ onto the detector defines one elementary shadow region $20_x$. Each elementary shadow region extends about a central point. Advantageously, the spacing between the central points of two adjacent elementary shadow regions is comprised between 1 and 10 cm, and preferably comprised between 1 cm and 5 cm. By projection, what is meant is a projection in the direction of propagation of the radiation emitted by the source.

Figure 1B:
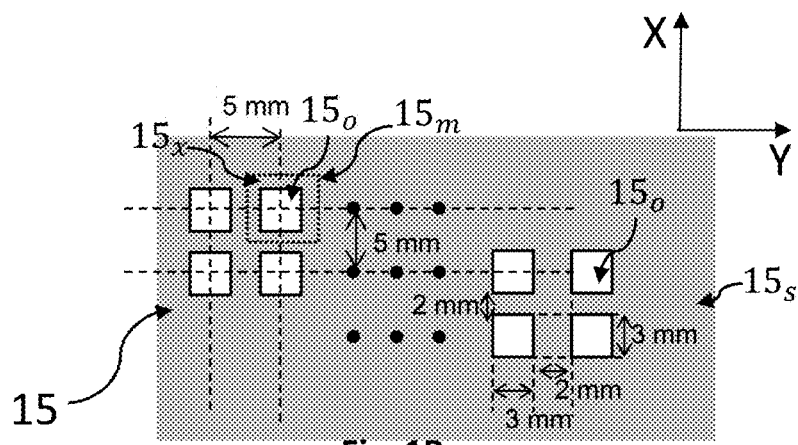
FIG. 1B represents a detail of a mask forming part of the device.

An example of a mask is shown in FIG. 1B. In this example, the mask comprises a regular arrangement of square apertures $15_o$ formed in an absorbent plate. The mask 15 forms a grid, comprising a regular arrangement of grid cells, each grid cell $15_m$ extending about one aperture $15_o$. In FIG. 1B, one grid cell $15_m$ has been shown by a dotted outline. The mask comprises absorbent elements $15_x$, each absorbent element representing the outline of one aperture $15_o$, inside a grid cell $15_m$. In this example, each aperture $15_o$ is a parallelepipedal land, the area of which, depending on the surface $15_s$ over which the mask extends, is 3 mm*3 mm, the spacing between the center of each aperture $15_o$ respectively being 5 mm in a Y-first direction and 5 mm in an X-second direction perpendicular to the first direction. In this example, the material from which the mask is made is graphite, of 5 mm thickness. Thickness means in a direction perpendicular to the area over which the mask extends. Generally, the mask is made of a material that is absorbent enough to attenuate a sufficient amount of the primary radiation. However, materials that are excessively dense, such as heavy metals, lead for example, which are liable to produce significant scattering of the incident radiation before the latter reaches the object, are to be avoided. Among the preferred constituent materials of the mask, mention may be made, in addition to graphite, of aluminum, copper, or boron.

Other geometries may be envisaged. For example, dense lands separated by free spaces, as described in EP3153888, are one option. It is also possible to envisage the spacing between the various absorbent elements being irregular, or each absorbent element having an irregular geometry.

The apertures $15_o$ formed in the mask 15 are made of a material considered to be transparent with regard to the photons, in the energy range in question. It is for example a question of air. It may also be a question of a small thickness of a plastic, of paper or of a light metal such as aluminum, iron, or copper. Thus, in each aperture $15_o$, the attenuation coefficient, as defined above, is preferably less than 0.5, or even 0.2 or even 0.1, and more generally sufficiently low to be neglected.

The number of apertures $15_o$ is dimensioned so as to cover the field of observation of the detector.

The mask 15 is interposed between the source 11 and the detector 20. Its projection, onto the detector, in the direction of propagation of the incident radiation $I^0$, defines shadow regions $20_x$, each shadow region encompassing those pixels of the detector $20_{i \in 20_x}$ that are aligned with each absorbent element $15_x$, in the direction of propagation of the radiation reaching the detector. More precisely, as mentioned above, the projection of each absorbent element $15_x$, in the direction of propagation of the incident radiation, forms a shadow region $20_x$ on the detector. The index x designates the shadow region in question. The pixels $20_{i \notin 20_x}$ not belonging to a shadow region $20_x$ receive radiation that is not attenuated by the absorbent elements $15_x$, whereas each pixel $20_{i \in 20_x}$ belonging to a shadow region receives radiation that has been attenuated by an absorbent element $15_x$, the latter being located on a line extending between said pixel and the radiation source 11.

The device also comprises a computing unit, or processor 21, a microprocessor for example, that is able to process each spectrum $S_i$ measured by the pixels of the detector. In particular, the processor is a microprocessor linked to a programmable memory 22 in which there is stored a sequence of instructions for performing the spectra processing and computing operations described in this description. These instructions may be saved on a processor-readable storage medium such as a hard disk, CD-ROM or other type of memory. The processor may be connected to a display unit 24, a screen for example.

One objective of the invention is to correct the spectrum $S_i$ measured by each pixel $20_i$, so as to decrease the scattered component $S_i^{diff}$ due to the object 10 and to establish a corrected spectrum $S_i^*$ such that $S_i^* \approx S_i'^P$ where $S_i'^P$ corresponds to the primary spectrum reaching the pixel in the absence of the mask 15 between the source 11 and the detector 20. In other words, the corrected spectrum $S_i^*$ corresponds to an estimate $\widehat{S'}_i^P$ of the primary radiation reaching the pixel $20_i$ without the mask interposed between the source and the detector: $S_i^* = \hat{S}_i'^P$.

Alternatively, it is possible to establish a corrected spectrum $S_i^*$ such that it corresponds to an estimate of the primary spectrum $\hat{S}_i^P$ reaching the object in the presence of the mask 15, but this is not generally a preferred alternative.

One objective of the invention is to evaluate the scattering spectrum $S_i^{diff}$ reaching the various pixels $20_i$ of the image sensor 20. In the exemplary embodiment described below, the scattering spectrum $S_i^{diff}$ is the spectrum of a scattered component of the spectrum $S_i$ measured by each pixel. The invention is based on an assumption that the scattering spectrum does not vary discontinuously along the detection plane P defined by the pixels. Therefore, it is possible to establish a priori a parametric, spatial scattering model $mod_K$ modeling a spatial dispersion of the scattering spectrum along the detection plane P. K corresponds to the parameters of the model. This model may for example be approximated by a spline function, i.e. a function defined, piecewise, by polynomials. The model is defined in spatial dimensions, corresponding for example to the X- and Y-axes of the detection plane P, and in a spectral dimension, reflecting the variation in the value of the spectrum as a function of energy. The application of the spatial model allows an estimate $\hat{S}_{i,K}^{diff}$ of the scattering spectrum to be obtained for each pixel $20_i$. Establishing and fitting the parametric model are important elements of the invention. An example is provided in the remainder of the description.

Another important element is the taking into account of a correction matrix $C_i$ defined for each pixel $20_i$, the correction matrix being representative of the attenuation of the incident radiation by the mask 15. The correction matrix allows a relationship to be established between the primary spectrum $S_i^P$ detected by a pixel $20_i$ and the primary spectrum $\hat{S}_i^{P'}$ that would be detected by the pixel $20_i$ in the absence of the mask. Thus, $\hat{S}_i^{P'} = C_i \times S_i^P$; where x designates the matrix product. The correction matrix $C_i$ takes into account the attenuation by each absorbent element of the mask, and imperfections in the detection of the pixel $20_i$. An example of determination of the correction matrix $C_i$ is presented in the remainder of the description.

Each pixel $20_i$ measures one spectrum $S_i$. Therefore, taking into account (1), it is possible to approximate that the primary spectrum $S_i^P$ measured by each pixel $20_i$ is such that:

$$S_i^P \approx S_i - S_i^{diff} \qquad (2).$$

Now, the spectrum $S_i^{diff}$ may be estimated by applying the spatial scattering model $mod_K$, so as to obtain an estimate $\hat{S}_{i,K}^{diff}$. Thus, from (2), it may be stated that:

$$S_i^P \approx S_i - \hat{S}_{i,K}^{diff} \qquad (3).$$

Applying the attenuation matrix $C_i$ to the primary spectrum $S_i^p$ measured by the pixel allows an estimate of the primary spectrum $\hat{S}_i^{p'}$ that would have been measured by each pixel $20_i$, in the absence of the mask, to be obtained according to the expression:

$$\hat{S}_i^{p'} = C_i \times (S_i - \hat{S}_{i,K}^{diff}) \qquad (4).$$

The symbol ' in the notation $\hat{S}_i^{p'}$ means that it is a question of the estimated primary spectrum in the absence of the mask 15. The primary spectrum $\hat{S}_i^{p'}$ that would be measured by each pixel $20_i$ in the absence of the mask 15 corresponds to the spectrum of the primary component $I_i^{p'}$ of the radiation $I_i$ measured by the pixel, in the absence of the mask.

It is assumed that locally, i.e. in the vicinity of each pixel $20_i$, in the absence of the mask, the primary component $I_i^{p'}$ does not fluctuate substantially. By vicinity of a pixel, what is meant is the pixels adjacent to said pixel. Thus, in the absence of the mask 15, the spatial gradient $\nabla \hat{S}_i^{p'}$ of the spectrum $\hat{S}_i^{p'}$ is low.

Therefore, the parameters K of the parametric scattering model may be determined by considering a cost function $\mathcal{F}(K)$ established using the spatial gradient $\nabla \hat{S}_i^{p'}$. The parameters K of the parametric scattering model are those that minimize the cost function $\mathcal{F}(K)$. In other words, the parameters K of the model are those that "erase" the traces of the mask from the spatial distribution of the spectrum $\hat{S}_i^{p'}$.

According to a first example, the cost function corresponds to the sum of the spatial gradient $\nabla \hat{S}_i^{p'}$ over a number $N_i$ of pixels and over a number $N_n$ of energy channels, such that:

$$\mathcal{F}(K) = \Sigma_{i,n}^{2N_i,N_n} f(\nabla \hat{S}_i^{p'}(n)) \qquad (5).$$

Namely $\mathcal{F}(K) = \Sigma_{j=1}^{2N_iN_n} f(\nabla C \times (S - \hat{S}_K^{diff})|_j) \qquad (5')$.

In (5'):

$f$ is a function, corresponding for example to a norm. It may for example be a question of a norm of order 1 or of a norm of order 2. $f$ may be a Huber or Charbonnier function, this type of function being able to be considered to approximate a norm of order 1.

$\nabla$ designates the spatial gradient operator, the spatial gradient being successively calculated in two orthogonal X- and Y-directions. It may be expressed in the form of a matrix of $(2N_iN_n; N_iN_n)$ size.

j is a super index, taking into account a spatial coordinate i of a pixel, a spectral coordinate n and a direction of computation of the gradient (along the X-axis or along the Y-axis).

S is a vector, of $N_iN_n$ size, formed by a concatenation of the measured spectra $S_i$.

$\hat{S}_K^{diff}$ is vector, of $N_iN_n$ size, formed by a concatenation of the estimated scattering spectra $\hat{S}_{i,K}^{diff}$.

C is a matrix of $(N_iN_n; N_iN_n)$ size, obtained by concatenation of all of the correction matrices $C_i$ defined for each pixel $20_i$.

Minimizing the cost function $\mathcal{F}(K)$ allows the parameters K of the spatial model of the scattered radiation to be obtained. In other words:

$$K = \underset{K}{\mathrm{argmin}}(\mathcal{F}(K)). \qquad (6)$$

Cost functions expressed in other ways, such that the parameters K of the model minimize or maximize the cost function, or make it tend toward a preset value, are possible.

Figure 2:
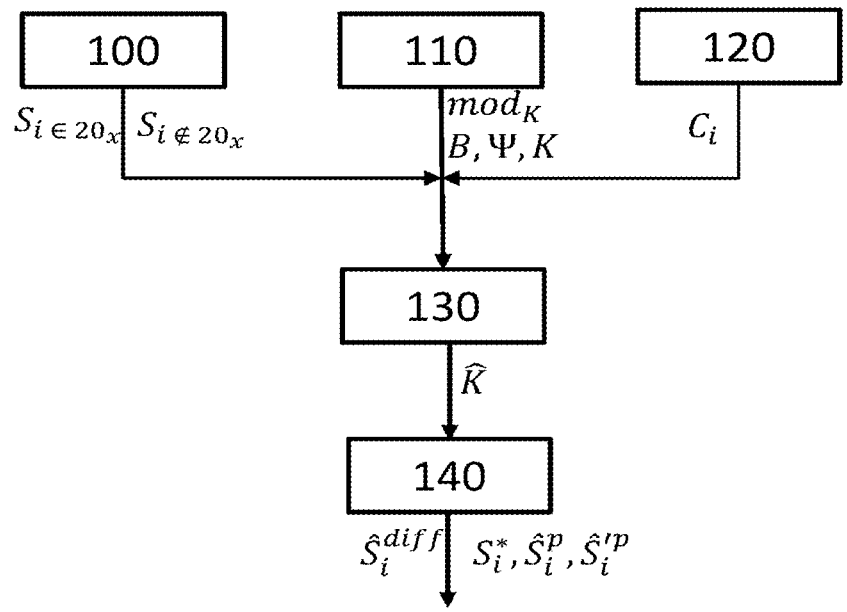
FIG. 2 shows the main steps of one embodiment of the invention.

The main steps of a method according to the invention will now be described with reference to FIG. 2.

Step 100: acquiring the spectra transmitted by the object. Each pixel $20_{i \in 20_x}$ in a shadow region $20_x$ acquires a spectrum $S_{i \in 20_x}$ transmitted by the object 10 and affected by an attenuation due to an absorbent element $15_x$. Each pixel $20_{i \notin 20_x}$ outside of a shadow region $20_x$ acquires a spectrum $S_{i \notin 20_x}$ transmitted by the object 10 but without the influence of an absorbent element $15_x$ of the mask 15.

Step 110: establishing the spatial scattering model $\mathrm{mod}_K$, conditioned by the parameters K.

The spatial scattering model comprises a spatial component, representative of the spatial variation in the scattering spectrum. It may also comprise a spectral component, representative of the spectral variation in the scattering spectrum.

As regards the spatial component, it may be expressed by a B-spline with 2 spatial dimensions, corresponding to the two X- and Y-axes defining the detection plane. The B-spline may be of order 2, with a gap between two nodes of 32 pixels, the nodes being distributed in the two dimensions of the detection plane.

Figure 1C:
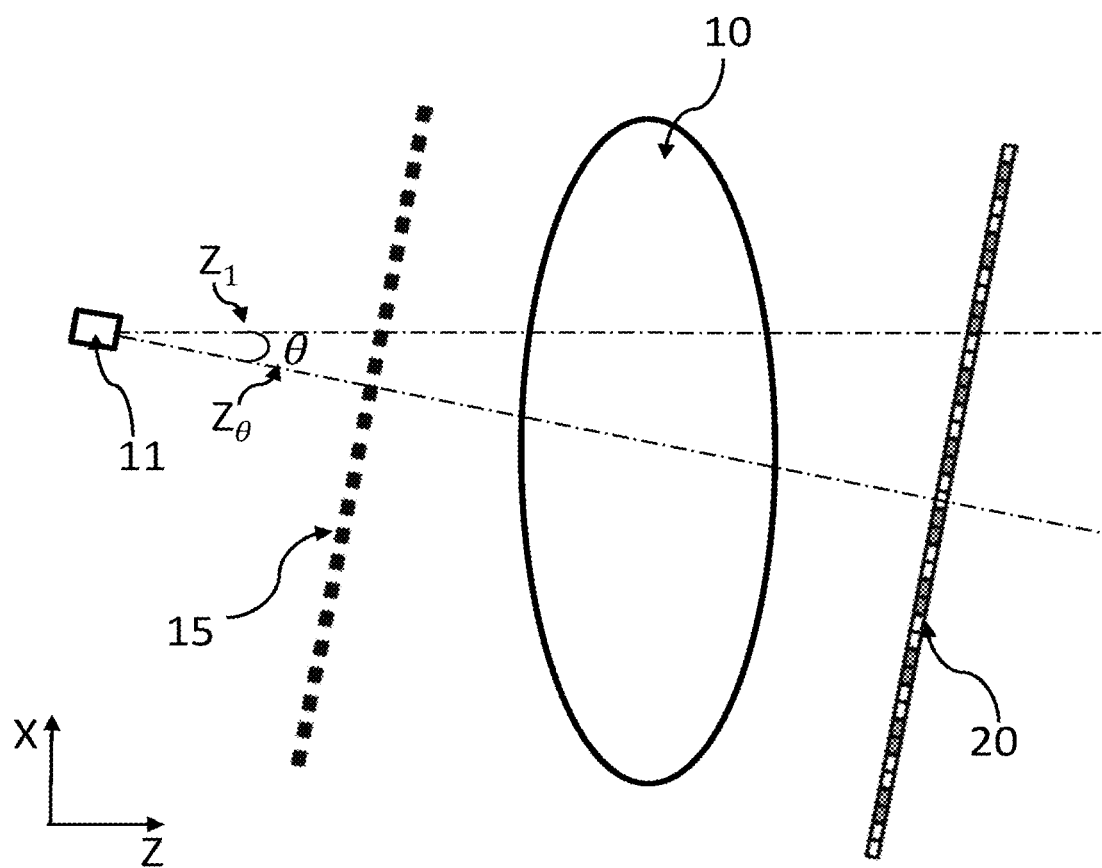
FIG. 1C illustrates a relative rotation of the detector and of the source with respect to the object.

According to one variant, described below, it is possible to take account of a rotation of the object with respect to the detector by a plurality of angles of rotation θ. Such a configuration is shown in FIG. 1C. In the configuration shown in FIG. 1A, the detector 20 lies perpendicular to an axis $Z_1$, parallel to the Z-axis. In the configuration shown in FIG. 1C, the detector 20 lies perpendicular to an axis $Z_\theta$. Between the two configurations shown in FIGS. 1A and 1C, respectively, the detector 20 and the source 11 have undergone a rotation of angle θ with respect to the object 10. This type of rotation is conventional in tomographic object reconstruction methods. When the detector is able to undergo a rotation with respect to the object, the spatial model may be expressed using a 3-dimensional B-spline (two dimensions corresponding to the detection plane and one dimension corresponding to the angle of rotation). Generally, the number of dimensions in which the spatial model is established corresponds to the number of degrees of freedom taken into account when modeling the scattered radiation.

We may define a spectral sub-model, representing the spectral component of the spatial model. In our example, the measured spectrum $S_i$ is binned into bins of adjacent channels before being processed by the processing unit. On account of the discontinuities that may appear between channels thus binned, a 0-order B-spline with an inter-node distance of 1 channel is employed.

The parameters of the model form a vector of parameters K, of $N_K$ size, corresponding to the number of nodes of the model.

Thus, the parametric model may be expressed in the form of a matrix product, such that $$\hat{S}_{i,K}^{diff} = B \times \Psi \times K \qquad (10) \text{ with:}$$

B is a matrix representing the spatial component of the spatial model, of $[N_i. N_n; N_{k_i}. N_n]$, size, . being the product operator;

Ψ is a matrix representing the spectral component (or spectral sub-model) of the spatial model, of $[N_{k_i}N_n; N_k]$ size; in this example, Ψ is the identity matrix. This means that the contents of the energy channels are independent of one another.

K is a vector of parameters containing the parameters of the model, of $N_k$ size;

$N_k$, is the number of spatial nodes considered in the model;

x is the matrix product.
Each term of the matrix B is such that:

$$B[i \cdot n; k_i \cdot n] = \beta^2\left(\frac{u - u_{k_i}}{\Delta_u}\right)\beta^2\left(\frac{v - v_{k_i}}{\Delta_v}\right) \qquad (10')$$

where:
- u and v designate the coordinates of the pixel $20i$ in the plane of the detector, along the X- and Y-axes, respectively;
- $u_{k_i}$ and $V_{k_i}$ denote the coordinates of the node of index $k_i$ in the plane of the detector;
- $\Delta_u$ and $\Delta_v$ are the distances between two consecutive nodes along the X-axis and the Y-axis, respectively;
- $\beta^2$ is a B-spline function, of order 2, with:

$\beta^2(w) = \frac{1}{2}(w^2 + 3w + 9/4)$ if $w \in [-3/2, -\frac{1}{2}[$;

$\beta^2(w) = 9/4 - w^2$ if $w \in [-\frac{1}{2}, +\frac{1}{2}[$;

$\beta^2(w) = \frac{1}{2}(w^2 - 3w + 9/4)$ if $w \in [\frac{1}{2}, 3/2[$;

$\beta^2(w) = 0$ for $w < -3/2$ or $w \geq 3/2$.

Step 120: establishing a correction matrix $C_i$ for each pixel $20_i$.

The attenuation by an absorbent element $15_x$ of the mask 15 may be taken into account via a correction matrix $C_i$ defined for each pixel $20_i$. For the pixels $20_{i \notin 20_x}$, the correction matrix is unitary. The correction matrix $C_i$ is described below for pixels $20_{i \in 20_x}$ located in a shadow region.

According to a first approximation, based on an assumption of a perfect detector, the correction matrix may be determined by constructing an attenuation matrix M, each term of which corresponds to an attenuation in a given energy range. More precisely, each term M(p, p)= $e^{-\mu_x \ell_x}$ (11), where
- $\mu_x$ is the linear attenuation coefficient, in the energy band $\Delta E_p$ associated with row p of the attenuation matrix M;
- $\ell$ is the thickness of the absorbent element $15_x$ the projection of which onto the mask 15 forms the shadow region $20_x$ in question.

Thus, not taking into account the response of the detector, or considering a perfect detector, $C_i = M^{-1}$.

Figure 3A:
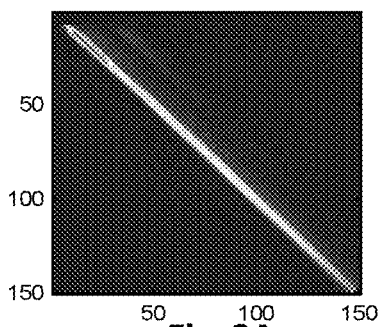
FIG. 3A shows a response matrix of the detector.

When the detector is not perfect, each pixel $20_i$ may be characterized by a response matrix $D_i$, representing the imperfections of the detection. An example of the response matrix, of N×M size, is shown in FIG. 3A. N is the number of channels n of each spectrum formed by the detector and M is the number of channels into which the spectrum incident on the detector is discretized. N and M are two positive integers. In this example, N=M=150, but, generally, the number of channels of the spectrum is higher than 2, or even higher than 10, and may reach several hundred. Each term $D_i(u, v)$ of the response matrix represents a probability that a photon incident on the detector, of energy v, is considered by the detector to have an energy u.

Figure 3B:
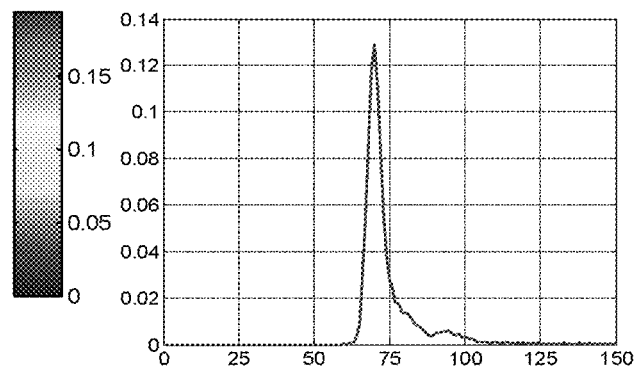
FIGS. 3B and 3C show a row and a column of this response matrix, respectively.
Figure 3C:
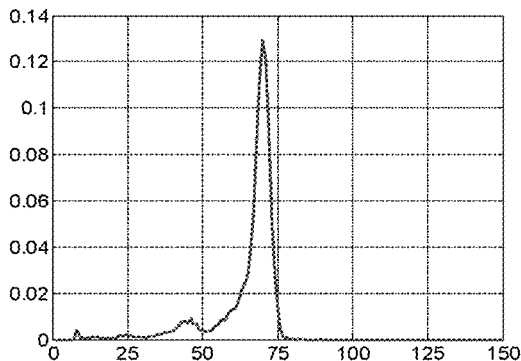

In other words, each row $D_i(u, \cdot)$ of the matrix, such as that shown in FIG. 3B, represents a probability distribution of the energy v of a photon reaching the detector when a photon of energy u is detected. FIG. 3B shows row 70 of the matrix $D_i$. Analogously, each column $D_i(\cdot, v)$ of the matrix, such as that shown in FIG. 3C, corresponds to a probability distribution of the energy u detected by the detector when the photon reaching the detector has an energy v. FIG. 3C shows column 70 of the matrix D. The finer the energy resolution of the detector, the more this matrix tends toward a diagonal matrix. In the case of a perfect detector, the matrix $D_i$ is the identity matrix.

Taking into account the imperfections of the detector, via the response matrix $D_i$, the correction matrix $C_i$ may be expressed as follows:

$$C_i = D_i \times M^{-1} \times D_i^{-1} \qquad (12).$$

That said, the response matrix $D_i$ is generally not invertible. In order to take into account the response of each pixel $20_i$ of the detector, the inventors have determined that the correction matrix $C_i$ should be a triangular matrix, of ($N_n$, $N_n$) size, and each term of which is such that:

$$C_i(p,q) = \alpha_{i,p} h(p-q)[\delta(1-\beta_{i,p}) - \beta_{i,p} e^{-\gamma_{i,p}(q-p)}] \qquad (13);$$

where:
- h is the Heaviside function;
- $\delta$ is the Dirac function;
- $\alpha_{i,p}$, $\beta_{i,p}$ and $\gamma_{i,p}$ are scalars determined in a calibrating phase. These scalars are associated with one pixel $20_i$.

The calibrating phase is carried out with no object 10 between the detector 20 and the source 11. It consists in acquiring:
- a spectral image, called the full-flux image $F^0$, with no mask 15 between the source 11 and the detector 20;
- a spectral image, called the masked image $M^0$, with the mask 15 interposed between the source 11 and the detector 20.

For each pixel $20_i$, the coefficients $\alpha_{i,p}$, $\beta_{i,p}$ and $\gamma_{i,p}$ are such that:

$$(\alpha_{i,p}, \beta_{i,p}, \gamma_{i,p}) = \operatorname*{argmin}_{\alpha_{i,p}, \beta_{i,p}, \gamma_{i,p}} \left| F_i^0(p) - \sum_{q=1}^{N_n} C_i(p,q) M_i^0(q) \right| \qquad (14)$$

where:
- $F_i^0(p)$ is the value of the full-flux spectrum $F_i^0$ measured by the pixel $20_i$ in the energy channel p.
- $M_i^0(q)$ is the value of the masked spectrum $M_i^0$ measured by the pixel $20_i$ in the energy channel q.

Figure 4A:
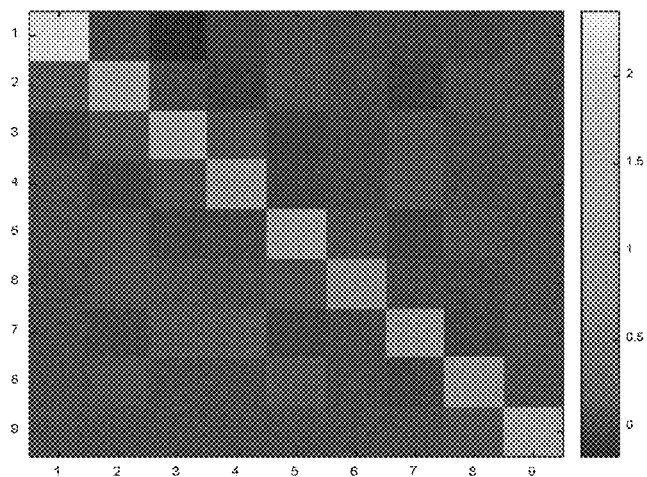
FIG. 4A is an example of a correction matrix established for a pixel.
Figure 4B:
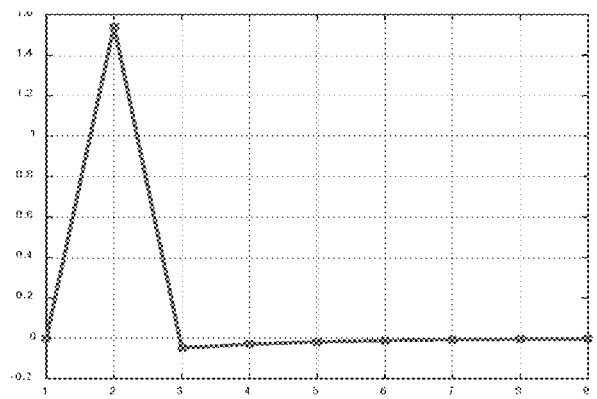
FIG. 4B shows a row of the correction matrix.

FIGS. 4A and 4B show an example of a correction matrix and a profile of the second row of this matrix, respectively.

Step 130: estimating the parameters K of the model.

Having defined the spatial model (step 110) parameterized by the vector K, and after having measured, with each of the pixels of the detector (step 100), the spectrum of the radiation transmitted by the object, the correction matrices $C_i$ defined for each pixel (step 120) are used to estimate the parameters K of the model. As mentioned with reference to expressions (5) and (6), the parameters of the model are estimated by minimizing a cost function. The cost function may be, for example:

$$\mathcal{F}(K) = \Sigma_{i,n}^{2N_i,N_n} f(\nabla \hat{S}_i^{j'}(n)) = \Sigma_{j=1}^{2N_iN_n} f([\nabla C \times (S - B \times \Psi \times K)]_j) \qquad (15)$$

C and S corresponding to matrices such as defined with reference to expression (5'), j being the superindex defined with reference to expression (5).

The function $f$ may be a Charbonnier function, with $$f(q) = \lambda^2 \sqrt{1 + \left(\frac{q}{\lambda}\right)^2} - 1,$$

(16), where $\lambda^2$ is a scalar parameter, with for example $\lambda=10^{25}$.

Thus the vector $\hat{K}$ such as $$\hat{K} = \underset{K}{\operatorname{argmin}} \mathcal{F}(K)$$

is estimated.

Step 140: correcting the spectrum measured by each pixel.

Estimating the vector $\hat{K}$ allows the scattering spectrum $\hat{S}_{i,K}^{diff}$ to be estimated, with:

$$\hat{S}_{i,K}^{diff} = B \times \Psi \times \hat{K} \qquad (17).$$

The spectrum $S_i$ measured by each pixel may be corrected to obtain a corrected spectrum $S_i^*$. The latter corresponds to an estimate $\hat{S}_i^P$ of the spectrum of the primary radiation transmitted by the object and detected by each pixel, so that:

$$S_i^* = \hat{S}_i^P = \hat{S}_i - S_i^{diff} \qquad (18), \text{ with } \hat{S}_i^{diff} = \hat{S}_{i,K}^{diff} \text{ or, preferably:}$$

$$S_i^* = \hat{S}'_i^P = C_i \times (S_i - \hat{S}_i^{diff}) \qquad (18').$$

According to one variant, the relative position of the detector with respect to the object varies. For example, the assembly, formed by the radiation source 11 and the detector 20, rotates around the object, as shown in FIG. 1C. Each position of the detector 20 with respect to the object 10 corresponds to one angle $\theta$. The spatial scattering model may take into account an angular variability of the scattering spectrum, in the form of a third spatial axis representing the angle $\theta$. If $N_\theta$ is the number of angular steps considered, the spatial model is such that:

$$\hat{S}_{i,K}^{diff} = B \times \Psi \times K \qquad (10) \text{ where:}$$

B is a matrix representing the spatial sub-model, of $[N_i \cdot N_n \cdot N_\theta; N_{k_i} \cdot N_n \cdot N_{k_\theta}]$ size;

$k_\theta$ is the number of angular nodes considered;

. is the product operator;

$\Psi$ is a matrix representing the spectral sub-model, of $[N_{k_i} \cdot N_n \cdot N_{k_\theta}; N_k]$ size;

K is a vector containing the parameters of the model, of $N_k$ size.

$$B[i \cdot n \cdot \theta; k_i \cdot n \cdot k_\theta] = \beta^2\left(\frac{u - u_{k_i}}{\Delta_u}\right)\beta^2\left(\frac{v - v_{k_i}}{\Delta_v}\right)\beta^2\left(\frac{\theta - \theta_{k_\theta}}{\Delta_\theta}\right)$$

where:

u and v designate the coordinates of the pixel 20*i* in the plane of the detector, along the X- and Y-axes, respectively;

$u_{k_i}$ and $V_{k_i}$ denote the coordinates of the node of index $k_i$ in the plane of the detector;

$\theta_{k_\theta}$ designates the angular coordinate of the node of index $k_\theta$;

$\Delta_u$ and $\Delta_v$ are the distances between two consecutive nodes along the X-axis and the Y-axis, respectively;

$\Delta_\theta$ is the separation between two consecutive angular nodes;

$\beta^2$ is a B-spline function, of order 2.

Expression (15) becomes:

$$\mathcal{F}_{(K)} = \Sigma_{i,n,\theta}^{2N_i,N_n,N\theta}[(\nabla S_{i,\theta}^P(n)) = \Sigma_{j=1}^{2N_iN_nN\theta}[(\nabla C \times (S - B \times \Psi \times K)]|_j \qquad (19).$$

Such an embodiment is relevant when acquiring images with a view to carrying out tomographic reconstruction. The spectrum $S_{i,\theta}$ corresponding to each angle $\theta$ may thus be corrected to reflect an estimate, at each angle, of the scattering spectrum, in the same way as explained with reference to expressions (18) and (18').

Methods such as described above may be optimized by giving priority to the information output by relevant pixels, or by only taking the latter into account, relevant pixels being those for which the implementation of the minimization algorithm is most effective.

Relevant pixels may be pixels adjacent to the borders bounding the shadow regions $\mathbf{20}_x$ defined by the mask 15. Relevant pixels may be determined from a two-dimensional gradient of the image $M^0$ of the mask: they correspond to the non-zero components of the gradient of the image of the mask. A weighting matrix W may be established, such that $W = \operatorname{diag}(\nabla M^0)$.

When the angular variation given by $\theta$ is not taken into account, W is a matrix of $2N_iN_n$; $2N_iN_n$ size. When the angular variation is taken into account, W is a matrix the size of which is $2N_iN_nN_\theta$; $2N_iN_nN_\theta$.

The weighting matrix W is taken into account when determining the cost function, such that:

$$\mathcal{F}_{(K)} = \Sigma_{j=1}^{2N_iN_n}[(WVC \times (S - B \times \Psi \times K)]|_j \qquad (20) \text{ or}$$

$$\mathcal{F}_{(K)} = \Sigma_{j=1}^{2N_iN_nN\theta}[(WVC \times (S - B \times \Psi \times K)]|_j \qquad (20').$$

Preferably, the relevant pixels must not be located on the edges of the object 10, or level with internal structures of the object that induce a high contrast in attenuation. Specifically, on the borders of the object, or when the object exhibits high local attenuation gradients, the primary spectrum transmitted by the object contains discontinuities. The assumption of local continuity in the primary spectrum, employed in the above algorithm, is then not appropriate. Pixels located facing the borders of the object or facing high local attenuation gradients are therefore considered not to be relevant and are not taken into account when establishing the cost function and minimizing it. Alternatively, pixels considered not to be relevant may be assigned a low weighting coefficient, such that the cost function essentially depends on pixels considered to be relevant.

Trials

Simulations have been carried out considering a radiation source 11 taking the form of an X-ray tube with a tungsten anode, the tube being subjected to a voltage of 120 kV, and filtered by a thickness of 0.25 mm copper and 8.4 mm aluminum. The detector 20 comprised 1024 (along the X-axis)*1024 (along the Y-axis) pixels, each pixel extending over an area of 400 μm×400 μm and over a thickness of 3 mm. The detector was energy resolved, and each pixel allowed spectra of 256 energy channels to be obtained. The pixels were binned spatially into bins of 16 adjacent pixels (4×4 binning). The spectrum acquired by each bin of pixels underwent energy binning so as to form 9 energy channels, with a spectral width of 10 keV, extending between 30 and 120 keV. The mask used was that shown in FIG. 1B.

FIGS. 5A, 5B and 5C respectively show simulated images of a skull. They respectively show a spatial distribution of the attenuation, the latter being obtained from:

the spectrum $S_i$ detected by each pixel, the reference primary spectrum $S_i^{p,ref}$ reaching every pixel. The reference primary spectrum was obtained by modeling.

the corrected spectrum $S_i^*$ according to the invention. The corrected spectrum corresponds to an estimate $\hat{S}'_i^P$ of the primary spectrum of the radiation transmitted by the object in the absence of the mask. The closer the estimated primary spectrum $\hat{S}'^p_i$ gets to the reference primary spectrum $S^{p,ref}_i$, the better the correction.

In each of these cases, the attenuation was obtained, for each pixel, by performing the integral, over the energy channels, of the spectrum in question. Thus, respectively the attenuation shown in FIGS. 5A 5B and 5C corresponds to $$-\ln\left(\frac{\sum_{n=1}^{N_n} S_i(n)}{\sum_{n=1}^{N_n} S_{i,0}(n)}\right),$$

$$-\ln\left(\frac{\sum_{n=1}^{N_n} S^{p,ref}_i(n)}{\sum_{n=1}^{N_n} S_{i,0}(n)}\right) \text{ and } -\ln\left(\frac{\sum_{n=1}^{N_n} \hat{S}'^p_i(n)}{\sum_{n=1}^{N_n} S_{i,0}(n)}\right).$$

$S_{i,0}$ corresponds to the spectrum, measured by a pixel $20_i$, of radiation $I_0$ reaching the detector in the absence of the object.

In FIG. 5A, the spectrum considered to estimate the attenuation contained a large scattered-radiation component. This results in an underestimation of the attenuation. FIGS. 5B and 5C are consistent, and show a higher attenuation than in FIG. 5A. This is because the attenuation was estimated only on the basis of an estimate of the primary spectrum, i.e. the spectrum of the primary radiation transmitted by the object and reaching the detector.

FIG. 5D shows profiles of the attenuation along a horizontal line shown in FIGS. 5A, 5B and 5C. The spectra a, b and c correspond to the spectra of FIGS. 5A, 5B and 5C, respectively.

FIG. 5E shows, at the level of the central pixel of the detector 20, curves representing the spectral line attenuation, the latter being obtained from the ratios $$-\ln\left(\frac{S_i}{S_{i,0}}\right) \text{(curve } a\text{)},$$

$$-\ln\left(\frac{S^{p,ref}_i}{S_{i,0}}\right) \text{(curve } b\text{) and } -\ln\left(\frac{\hat{S}'^p_i}{S_{i,0}}\right) \text{(curve } c\text{)},$$

respectively. The correction effect achieved via the invention is once again observed: passage from the spectrum of curve a to the spectrum of curve c. The reference curve, corresponding to the spectral attenuation, is the curve b.

The invention may be applied in spectral imaging methods using ionizing radiation and in particular X-rays or gamma rays, for medical applications or, more generally, in the non-destructive testing of objects with the aim of investigating the internal structure of said objects. The object may be, for example, a piece of luggage, an industrial product, a structural element of an installation, for example a pipe, nuclear waste, or an aeronautical component, etc.

The invention allows the primary component of radiation to be estimated, thus limiting the influence of scattered radiation. The quality of the obtained image, and in particular its spatial resolution, is thus improved. The quantification of the attenuation produced by the object is more precise, this allowing a better estimate of the composition of the object examined. This results in results that are more precise, and more consistent with the object examined.

The invention claimed is:

1. A method for correcting a spectral image formed by ionizing electromagnetic radiation transmitted by an object, the object being placed between a radiation source and a detector, the radiation source being configured to emit incident ionizing electromagnetic radiation toward the object;

the detector comprising pixels, each pixel being configured to detect ionizing electromagnetic radiation transmitted by the object to the detector, and to measure an energy spectrum thereof, the transmitted ionizing electromagnetic radiation comprising scattered radiation caused by scattering of the incident ionizing electromagnetic radiation in the object and primary radiation; and a mask being interposed between the radiation source and the object, the mask comprising absorbent elements configured to attenuate one portion of the incident ionizing electromagnetic radiation, a projection of each absorbent element onto the detector forming one shadow region, such that the detector comprises a plurality of shadow regions that are spaced apart from one another, each shadow region corresponding to at least one pixel;

the method comprising:

a) irradiating the object and measuring, using the pixels of the detector, an energy spectrum representative of the ionizing electromagnetic radiation transmitted by the object;

b) defining a spatial model of an energy spectrum of the scattered radiation, so as to obtain, for various pixels of the detector, an estimate of the energy spectrum of the scattered radiation detected by each pixel, the spatial model being defined by parameters;

c) taking into account a cost function, the cost function being defined for various pixels and taking into account, for each pixel, a spatial variation in an estimate of an energy spectrum of the primary radiation that would be transmitted by the object in an absence of the mask, the estimate of the energy spectrum of the primary radiation in the absence of the mask being obtained by comparing, for each pixel:

the energy spectrum measured by each pixel in a), and an estimate of the energy spectrum of the scattered radiation, wherein the estimate is obtained using the spatial model resulting from b);

d) determining the parameters of the spatial model, for which the cost function is minimal or maximal;

e) for at least one pixel, estimating the energy spectrum of the scattered radiation reaching each pixel, by applying the determined parameters of the spatial model resulting from d); and for at least one pixel, correcting the energy spectrum measured in a) using the estimate of the energy spectrum of the scattered radiation resulting from e), so as to obtain a corrected energy spectrum corresponding to an estimate of the energy spectrum of the primary radiation reaching each pixel.

2. The method of claim 1, wherein the pixels of the detector lie in a detection plane, and wherein the spatial model is defined along two axes defining the detection plane.

3. The method of claim 2, wherein:

a) is implemented in a plurality of configurations, each configuration being associated with one orientation of the detector with respect to the object, so as to measure, using each pixel, energy spectra corresponding to various orientations; and the spatial model defined in b) takes into account a variation in the energy spectrum of the scattered radiation as a function of an orientation of the detector with respect to the object.

4. The method of claim 1, wherein, in c), the primary radiation transmitted by the object to each pixel, in the absence of the mask, is estimated by applying a correction matrix, defined for each pixel, to a difference between:
the energy spectrum measured by each pixel in a); and
an estimate of the energy spectrum of the scattered radiation, wherein the estimate is obtained using the spatial model resulting from b).

5. The method of claim 4, further comprising:
obtaining the correction matrix in a calibrating phase, with no object between the radiation source and the detector, according to the following calibrating operations:
irradiating the detector with and without the mask interposed between the radiation source and the detector, so as to obtain, for each pixel, a masked energy spectrum and a full-flux energy spectrum, respectively;
taking into account a parametric function in order to determine terms of the correction matrix, the parametric function depending on the parameters; and
taking into account the masked energy spectrum and the full-flux energy spectrum to determine the parameters of the parametric function, so as to determine the terms of the correction matrix;
wherein the correction matrix is triangular.

6. The method of claim 1, wherein the spatial model of the energy spectrum of the scattered radiation is expressed as a product of:
a matrix representative of a spatial distribution of the scattered radiation, and
a vector of parameters comprising the parameters of the spatial model;
wherein d) comprises estimating the vector of parameters.

7. The method of claim 1, wherein b) comprises defining a spectral model of the scattered radiation in order to take into account, in each pixel, a spectral variation of the scattered radiation, such that the spatial model and spectral model are defined by a vector of parameters.

8. The method of claim 7, wherein the spatial model and the spectral model may be expressed as a product of:
a matrix representative of a spatial distribution of the scattered radiation;
a matrix representative of the spectral variation of the scattered radiation; and
the vector of parameters;
wherein d) comprises estimating the vector of parameters.

9. The method of claim 1, wherein each absorbent element of the mask is configured to absorb between 5% and 80% of the incident ionizing electromagnetic radiation to which it is exposed, in a predetermined energy band.

10. The method of claim 1, wherein a) comprises normalizing the energy spectrum of the ionizing electromagnetic radiation transmitted by the object and measured by each pixel by an energy spectrum measured by each pixel with no object placed between the radiation source and the detector.

11. The method of claim 1, wherein, the mask extending over an area, each absorbent element is distant from another absorbent element by a distance of smaller than 1 cm.

12. A non-transitory data-storage medium comprising instructions that, when executed by a microprocessor, execute b) to f) of the method of claim 1, based on the energy spectrum measured in a).

13. A device for acquiring spectra of radiation transmitted by an object, comprising:
a radiation source configured to emit incident ionizing electromagnetic radiation toward the object;
a detector comprising pixels, each pixel being configured to detect ionizing electromagnetic radiation transmitted by the object to the detector, and to acquire an energy spectrum thereof;
a mask, configured to be interposed between the radiation source and the object, the mask comprising absorbent elements, the absorbent elements being configured to absorb a portion of the incident ionizing electromagnetic radiation, and a projection of the absorbent elements onto the detector defining shadow regions that are distant from one another; and
a processor, configured to receive the energy spectrum acquired by each pixel, and to implement b) to f) of the method of claim 1.

* * * * *